United States Patent [19]

Thomsen et al.

[11] Patent Number: 4,481,293

[45] Date of Patent: Nov. 6, 1984

[54] METHOD FOR THE PRODUCTION OF METHANE

[75] Inventors: Ove Thomsen, Växjö; Peter Rönnow, Mölnlycke, both of Sweden

[73] Assignee: A-Betong AB, Växjö, Sweden

[21] Appl. No.: 399,810

[22] Filed: Jul. 19, 1982

Related U.S. Application Data

[62] Division of Ser. No. 170,673, Nov. 6, 1979, Pat. No. 4,356,269.

[30] Foreign Application Priority Data

Mar. 6, 1978 [SE] Sweden ............................. 7802501

[51] Int. Cl.$^3$ ............................................... C12P 5/02
[52] U.S. Cl. .................................................. 435/167
[58] Field of Search ............... 435/314, 315, 316, 801, 435/813, 819, 167; 210/180, 195.1, 258, 603, 613; 71/10, 12, 23

[56] References Cited

U.S. PATENT DOCUMENTS

| | | | |
|---|---|---|---|
| 1,880,772 | 10/1932 | Buswell et al. | 435/316 X |
| 1,930,457 | 10/1933 | Prüss | 210/613 |
| 3,383,309 | 5/1968 | Chandler | 210/612 X |
| 3,954,565 | 5/1976 | Boiko et al. | 435/314 |
| 3,957,585 | 5/1976 | Malick | 435/314 X |
| 3,959,125 | 5/1976 | Teletzke | 210/603 |
| 3,984,286 | 10/1976 | Malick | 435/314 |
| 4,057,401 | 11/1977 | Boblitz | 71/10 X |
| 4,100,023 | 7/1978 | McDonald | 435/167 |
| 4,193,873 | 3/1980 | Thrasher | 210/180 X |
| 4,238,337 | 12/1980 | Peters et al. | 435/316 X |

FOREIGN PATENT DOCUMENTS

| | | |
|---|---|---|
| 3102720 | 9/1982 | Fed. Rep. of Germany ...... 435/167 |
| 2409305 | 7/1976 | France ................. 435/167 |
| 2481874 | 11/1981 | France ................. 435/167 |
| 0142635 | 10/1953 | Sweden . |
| 0395441 | 8/1977 | Sweden . |

*Primary Examiner*—Esther M. Kepplinger
*Assistant Examiner*—William J. Herald

[57] ABSTRACT

Method for producing methane by first heating and mixing an organic substrate to 70° C. and cooling same with fresh substrate to 50°-60° C. in an antechamber, transferring same to a processing chamber in the presence of methane-producing anaerobic microorganisms and therein cultivating the substrate under anaerobic conditions to produce methane.

1 Claim, 6 Drawing Figures

FIG. 6

METHOD FOR THE PRODUCTION OF METHANE

This is a division of application Ser. No. 170,673, filed Nov. 6, 1979, now U.S. Pat. No. 4,356,269.

TECHNICAL FIELD

The present invention relates to a method for the production of methane from a substrate comprising an organic material, by way of example manure, in a process by means of a culture of anaerobic and preferably thermophile microorganisms, which in a processing chamber is brought into contact with the organic material and in which the generated gas is collected.

The present invention also relates to a plant comprising a receptacle including a chamber forming a processing chamber and intended to enclose a substrate containing the culture of microorganisms, and in the upper portion of the chamber means for the removal of the gas from said space.

BACKGROUND ART

Methane ($CH_4$) is known as a useful source of energy for heating purpose and as fuel for internal combustion engines for the driving of working machines or for the production of electric power. By means of anaerobic microorganisms methane can be produced with a biological mass as substrate. As biological material can for example manure from cowsheds or swineries, vegetable or animal waste from farms and food-production industries be used. Also sewer sludge can be utilized, if it substantially contains organic material. In order to carry out the process, there are certain requisites, which are important to fulfil in order to obtain a high yield of gas, a reasonable processing time, a high plant utilization factor, and low handling costs, viz.:

(1) The process should be continuous, so that the culture of the microorganisms can be maintained for an uninterrupted gas production;
(2) Biological material should be continuously supplied and removed, so that the capacity of the plant due to volumetric efficiency can be utilized to the greatest possible extent, and any periods of standstill for supply and removal of material will not be required;
(3) The process should take place at such a temperature that a reasonable processing time and a high gas yield will be obtained;
(4) The handling of material should be automatic, preferably by means of pumps and not involve any essential manual labour.

Especially in large plants of capacity in the order of a few or several hundred cubic meters of substrate, these requisites have turned out to be difficult to fulfil by the technique of the prior art. Thus, a heating is necessary by use of types of anaerobic microorganisms, which in plants of the said size means a considerable sacrifice of costs with respect to construction and energy.

TECHNICAL PROBLEM

It is an object of the present invention to provide a method for the production of methane from cultures of microorganisms from organic waste, by means of which method said requisites are fulfilled.

It is another object to provide a plant, which is simple in operation, by means of which said method can be carried out.

SOLUTION

The object of the invention is obtained by means of a method according to the present invention which is characterized by that the substrate is introduced into an ante-chamber for pretreatment which is provided with heating means with the substrate heated in the pre-chamber to at least the temperature that it is intended to have during the process or preferably to a higher temperature, whereafter it is transported to the processing chamber and brought into contact with the culture of microorganisms. Said objects are also reached by means of a plant which is characterized by a second chamber with a separate space forming an ante-chamber and including means for the introduction of fresh substrate means for heating the substrate, and means for the transport of the treated substrate to the first said chamber for the supply for the fresh, heated substrate to the substrate containing the culture of microorganisms.

BRIEF DESCRIPTION OF DRAWINGS

Four embodiments of the installation according to the invention are illustrated in the accompanying drawings.

BEST MODE OF CARRYING OUT THE INVENTION

Figure 1:
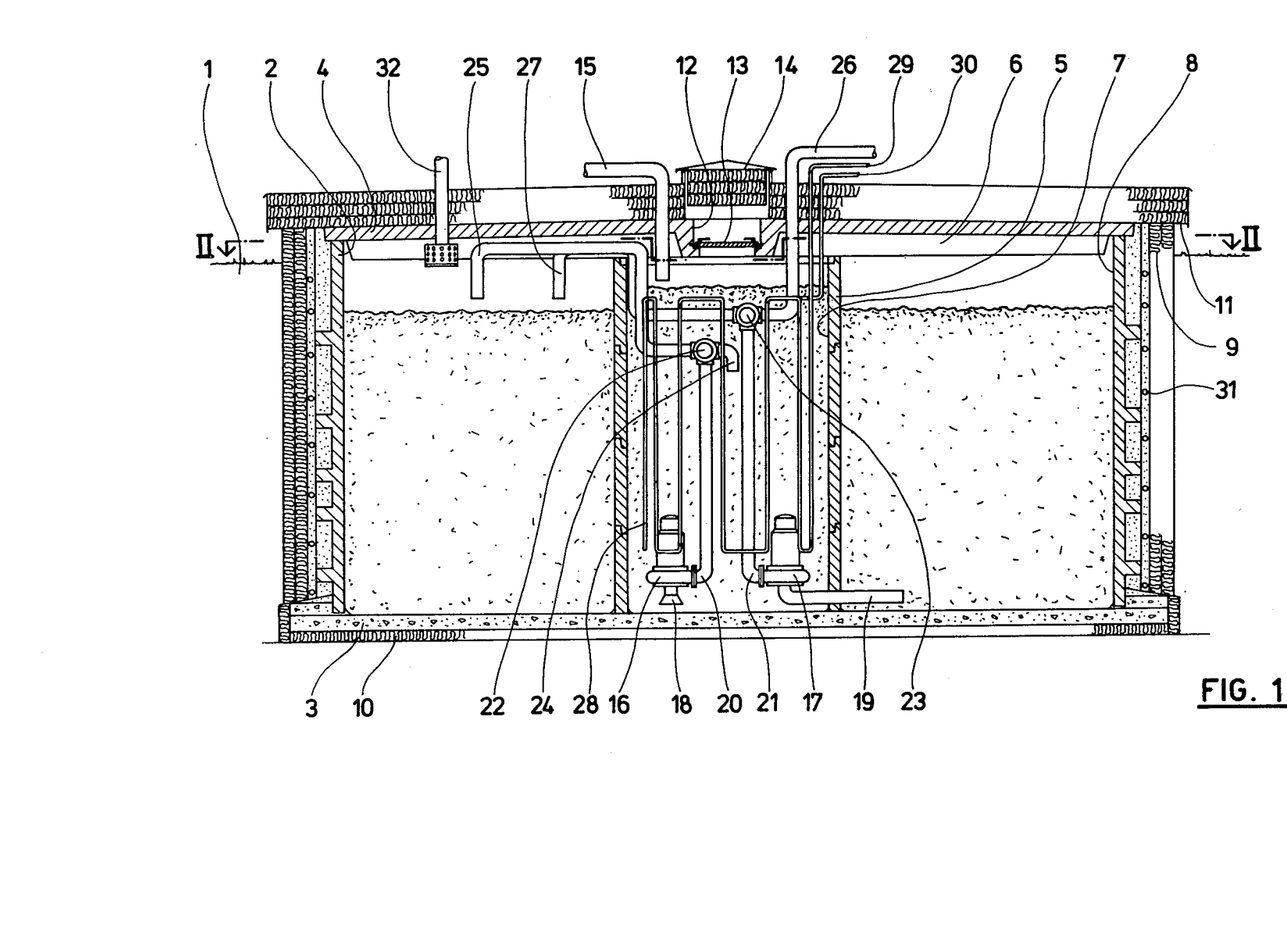
FIG. 1 shows a central vertical cross-section of a first embodiment of the plant according to the invention.

According to FIG. 1 the plant according to the first embodiment comprises a cylindric receptacle with an external wall 2, bottom plate 3 and a lid 4 divided into sections, which receptacle is suitably submerged in the surrounding ground 1. The parts 2 and 4 of the receptacle are made in the form of concrete elements, whereas the bottom 3 is suitably cast on the site. An annular wall 5 is concentrically placed in relation to the external wall 2, said wall 5 also being made of concrete and resting upon the bottom 3 and by means of end flanges 6 on its sections supporting the sections of the lid 4. Thus, the walls 2 and 4 form two spaces, a central chamber 7 inside the wall 5 and an annular chamber 8 between the walls 2 and 5.

An insulating layer 9, 10 and 11, which can be provided with a covering is applied to the outside of the wall 2, the bottom 3 and the lid 4 respectively. The sections of the lid 4 do not completely meet each other, but in between them form a central opening 12, which is covered with a lid 13 and an insulated hood 14 above the same. The lid 13 is an inspection cover. The lid 4 with the lid 13 tightly close the chambers formed by the chambers 7 and 8. As is shown the chambers 7 and 8 can be in communication with each other or else separated by the wall 5 extending up to the lid.

An inlet pipe 15 coming from the outside debouches in the chamber 7 inside the wall 5. Inside the chamber 7 there is a transportation system serving the purpose to displace the biological mass, viz. a first pumping device 16 and a second pumping device 17, each one comprising an electrically driven pump, by way of example of the centrifugal type. A short inlet feed pipe 18 of the pumping device 16 debouches directly in the chamber 7 at its bottom edge, whereas an inlet pipe 19 of the pumping device 17 debouches in the chamber 8. Pipes 20 and 21 extend from the respective outlet sides of the pumping device to motor valves 22 and 23 respectively. The motor valve 22 can be changed over so that it either can connect the pipe 20 with an outlet pipe 24 debouching in the chamber 7 or an outlet pipe 25 debouching in the chamber 8. The valve 23 is provided to connect the pipe 21 by means of either a pipe 26 debouching from the plant as described or a tube 27 debouching in the chamber 8.

In the chamber 7 is further a tube loop 28 provided, which is intended to serve as a heating coil, and which by means of an inlet pipe 29 and an outlet pipe 30 is in connection with a heating apparatus. Water is suitably used as heating medium and is by way of example brought to circulate from a boiler through the tube loop 28. There is an additional heating source, viz. a heating cable 31 located between the wall 2 and its insulation 9.

Further more an outlet pipe 32 for gas extends through the lid 4 and debouches in the chamber 8 close to the lid 4 and is in connection with a station for the utilization and/or storage of gas.

Figures 2, 3:
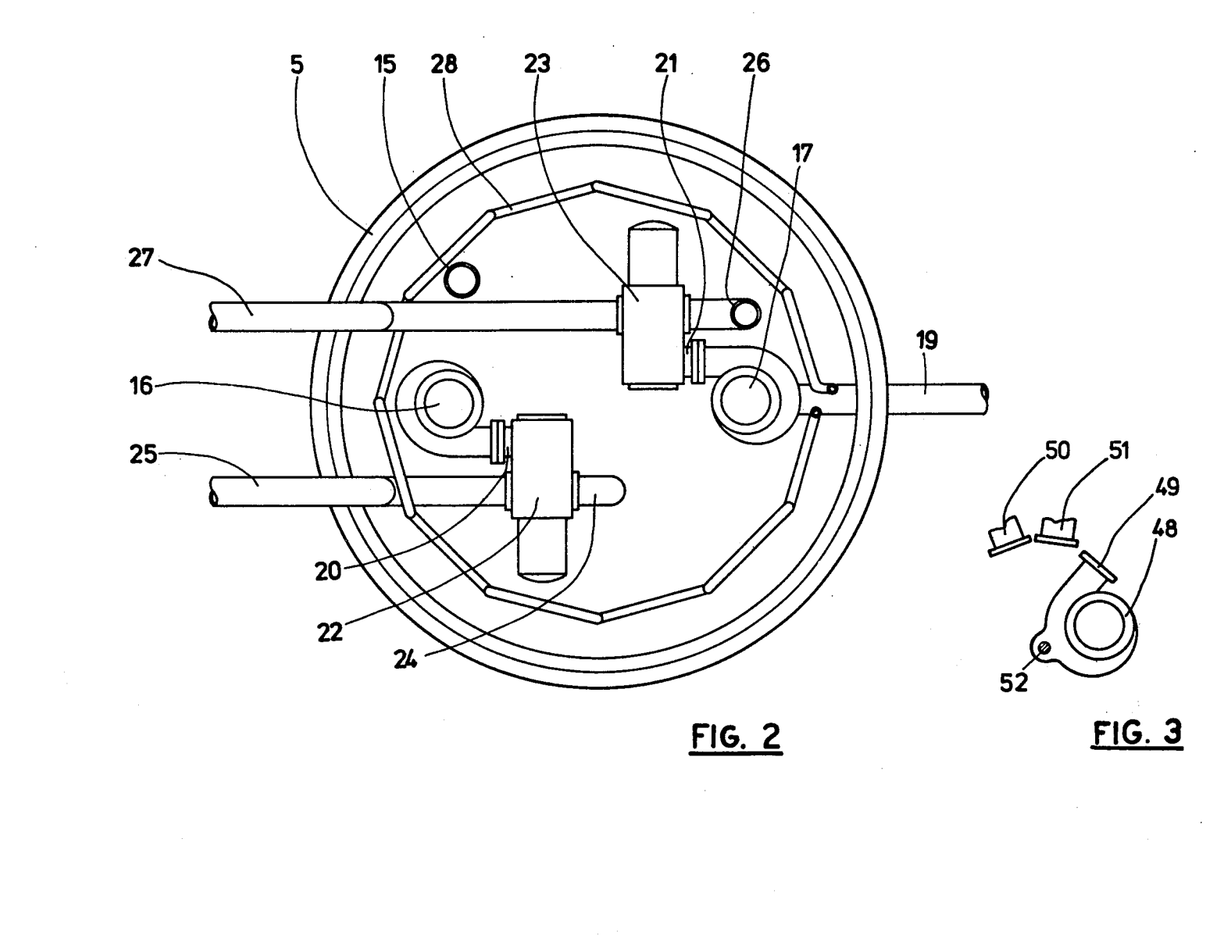
FIG. 2 shows the same embodiment along the line II—II in FIG. 1.
FIG. 3 shows in a variant a detail and FIGS. 4, 5 and 6 illustrate the second, the third and the fourth embodiment respectively in central cross-sectional views.

The transportation means and the heat loop described are also shown as seen from above on an enlarged scale in FIG. 2. A varied embodiment of the transportation means is shown in FIG. 3. In this variant a pump 48 (seen from above in FIG. 3) is placed in the chamber 8 at a peripherically located point of the bottom of the same. Two pipes 50 and 51 are debouching right in front of the short outlet feed pipe 49. The pump 48 has its inlet from the underside which is at a certain distance above the bottom. The pump can be pivoted round a shaft 52 extending in upwards direction through the lid 4. The pipe 50 in the same manner as the pipe 26 is stretching out from the plant and is a substitute for this pipe. The pipe 51 is stretching into the chamber 7. When the pump 48 is in the position shown, i.e. pivoted away from the pipes 50, 51, it can be used for producing a circulating pump effect in the mass in the chamber 8. If the pump 48 is pivoted into a position right in front of the pipe 51, mass can be returned to the chamber 7 in order to be heated. When removing mass from the chamber 8 the pump can be pivoted into a position right in front of the pipe 50, and the mass is thereby discharged from the plant when the pump is working. The supply of material to the chamber 7 as well as its circulation in the same by the pumping action and transfer to the chamber 8 is provided by means of a pump, which can be changed over by means of a valve, as has been described above.

Figure 4:
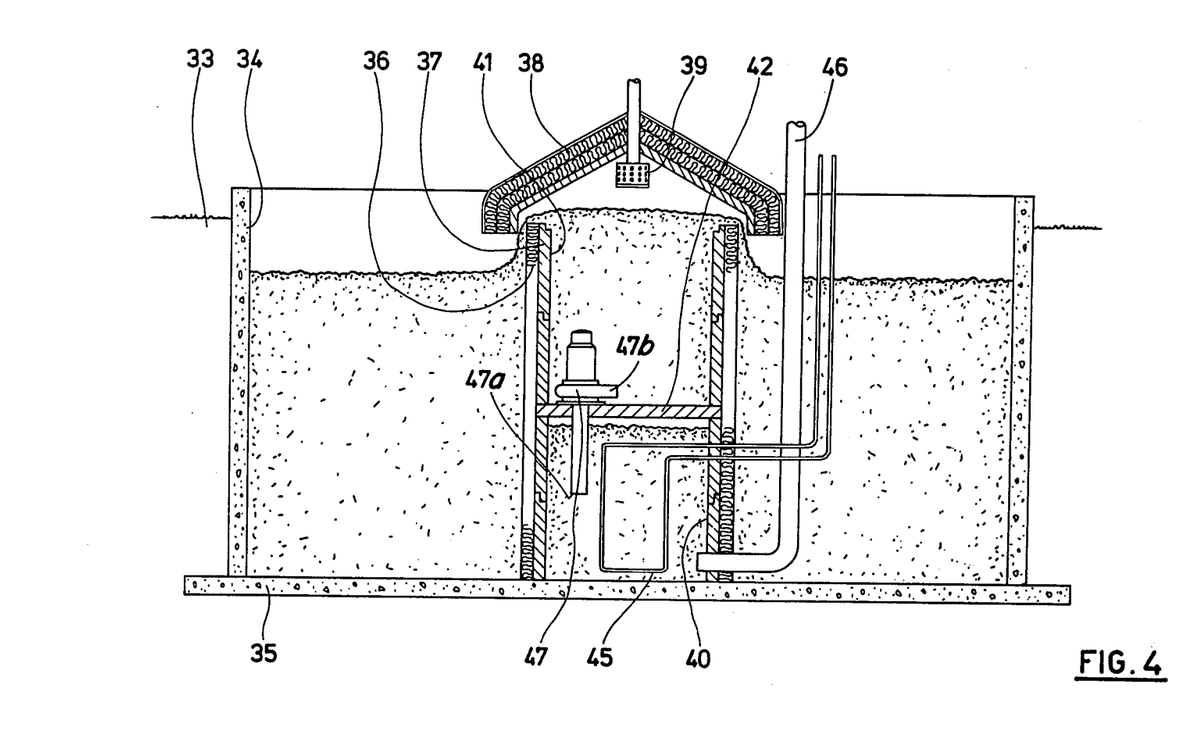
Figure 5:
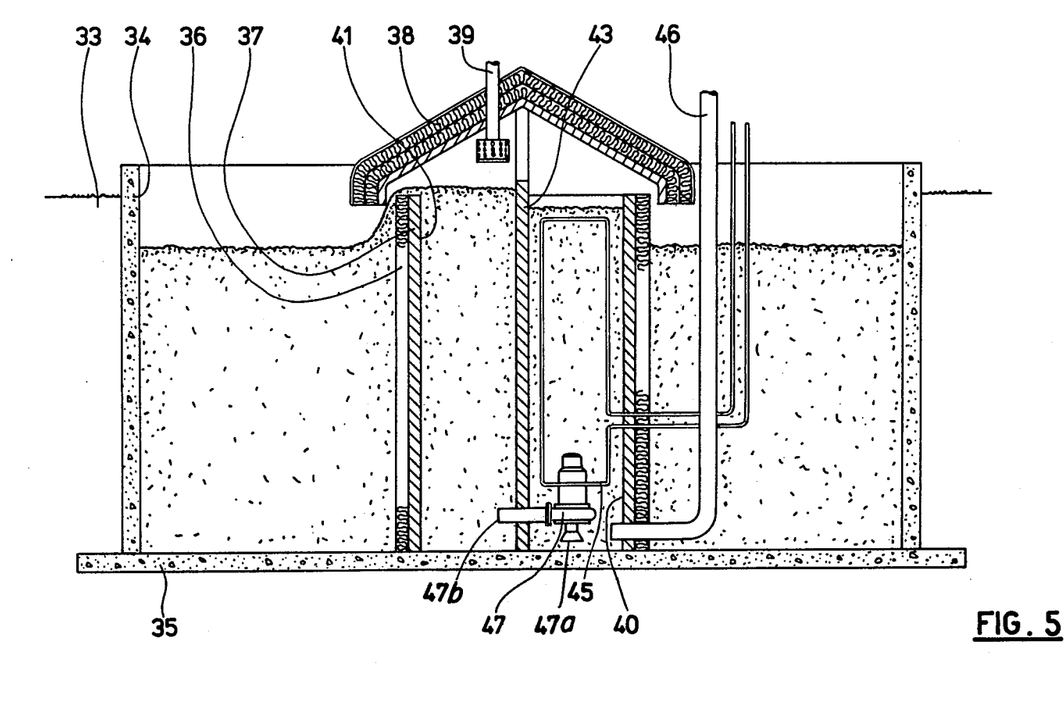
Figure 6:
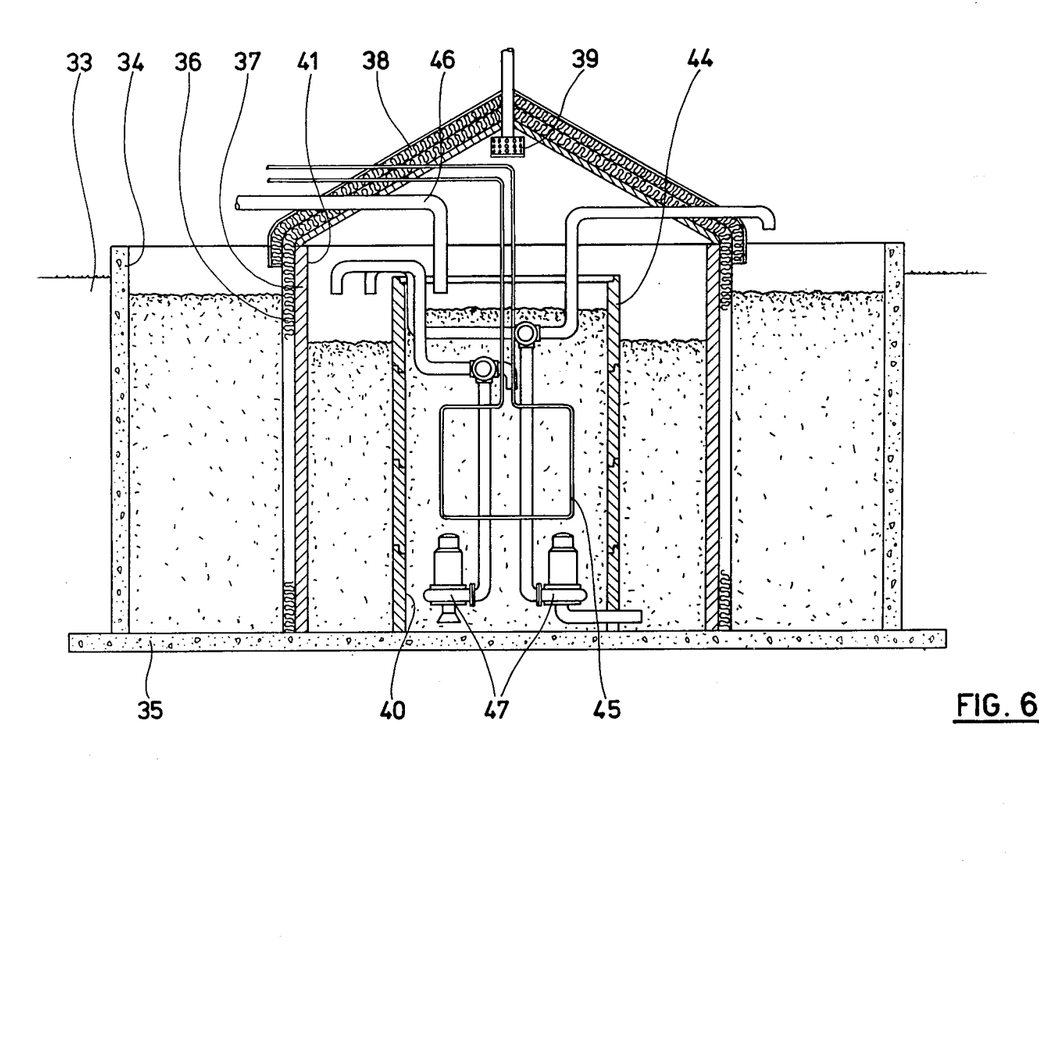

As is evident from the description the plant substantially comprises a first chamber represented by the chamber 7, in which a warming and transportation means is provided, and a second chamber represented by the chamber 8 and intended to enclose the biological material during the methane producing process itself. The embodiments according to FIGS. 4-6 are designed according to the same principle but with the difference that both chambers, accordingly the one provided with heating means and in the following called the ante-chamber and the second chamber in the following called the processing chamber, are placed in a greater space intended for storage of the biological material, which has been subjected to the gas producing process and which thereafter is intended to be used as fertilizer. Under practical conditions these embodiments may be used in order to serve as a supplementary gas producing plant for new or already existing manure yards of conventional design. What distinguishes the three different embodiments according to FIGS. 4-6 is the disposition of the gas producing device mounted in the manure yard in its two chambers.

Thus each one of the embodiments mentioned exhibits a manure yard preferably in the form of an excavation in the ground 33 and substantially comprising a wall 34 and a bottom 35. Suitably in a central position in this manure yard a wall 37 provided with an insulation 36 is installed together with an insulated roof 38 and the bottom 35 which assembly encloses the methane producing device. The produced gas is delivered from this device by means of a gas collection pipe 39. In all these embodiments the gas producing device is divided up in a ante-chamber 40 and a processing chamber 41. Said division is in the second embodiment according to FIG. 4 made by means of a horizontal wall 42, in the third embodiment according to FIG. 5 by means of a vertical wall 43, and in the fourth embodiment according to FIG. 6 by means of a circular vertical wall 44.

A heating loop 45 is installed in the respective ante-chamber 40, and an inlet pipe 46 for the biological material also ends in this chamber, which pipe can debouch at the bottom or in an upper portion of the chamber. In order to transfer material from the ante-chamber to the processing chamber all of the embodiments are provided with at least one pumping device 47 arranged to transport material from the pre-chamber 40 to the processing chamber 41. The transportation means, of which the pumping device is a part, in FIGS. 4 and 5 has been shown in its most simple embodiment exhibiting one single pump with an inlet pipe and an outlet pipe, whereas a more complicated embodiment is evident from FIGS. 1 and 6. The design of the transportation means is however not dependent upon the construction of the remaining part of the embodiments, but many combinations being possible.

It should finally be mentioned that the roof 38, which is of a hood-like design, in the embodiment according to FIG. 6 can enclose the device inside the wall 37 in a completely tight manner with the exception of the gas collection pipe 39 whereas in the embodiment according to FIGS. 4 and 5 an outflow of biological material shall take place from the processing chamber to the manure yard, the roof therefore is provided as a hood, which is open at its edge but folded down over the wall 37, in which hood the produced gas can be collected.

As mentioned, the material supplied can be of different kind. The plant shown in FIGS. 1 and 2 is planned for cowshed manure and intended to serve a fairly large stock of animals. The volume of the chamber 7 can be in the amount of 20 cubic meters and the volume of the chamber 8 of 200 cubic meters. The plants according to FIGS. 4-6 are also intended to be driven by means of cowshed manure, but they relate to a smaller stock of animals. The device for the production of methane is here limited to the chambers 40 and 41, whereas the space outside of these constitutes a storage space for the material, which already is processed. As examples of suitable volumes in such devices it can be mentioned 3 cubic meters for the space 40 and 30 cubic meters for the space 41. Because of the fact that the material in the space 35 does not take part in the process, the size of this space in the first hand depends upon the frequency of its removal. The manure for the process, which is supplied from a mechanized installation for manure feed, should have a proportion of dry substance of 10 to 15%, so called liquid manure. Even if the process is continuous, which means that the bacteriological process never is interrupted and an adequate quantity of material always is in the processing stage, this does not mean that the supply and also the removal of material can be discontinuous as long as at each opportunity only small part quantities of the whole mass will be handled. Thus the feed of the manure can be periodic, by way of example a few times per day, and the manure is then fed into the process.

As mentioned also other organic material than manure can be used. Parts of plants and vegetable waste and also slaughterhouse waste from by way of example food processing, deep freeze and canning industries can be utilized. Also sewer sludge can be used, if it does not contain any large proportion of non-biological material as sand, clay, industrial waste and similar. As a very suitable source so called water economizing water closet systems, for example vacuum systems, can be used, in which the water supply is very much limited, and where the water closet waste is kept apart from the waste water from households, industries and surface water.

If it is assumed that the plant is in operation, the ante-chamber 7 and 40 respectively is substantially filled with freshly introduced biological mass. This mass is supplied in a continuous or discontinuous sequence in the way mentioned through the inlet pipe 15/46 by means of a pumping device not shown. The culture of microorganisms intended for the methane production has then not yet been fed to the mass. A heating medium, by way of example hot water of a temperature of 60°–80° C. for warming of the biological mass is supplied to the tube loop 28/45 through the pipe 29. According to the speed of supply the material is fed out of the ante-chamber 7 and 40 respectively by means of the pumping device 18 and 47 respectively to the processing chamber 8 and 41 respectively.

By the transportation means according to FIGS. 1 and 2 the mass is introduced in the ante-chamber 7 via the inlet feed pipe 18 and is transported by means of the pump 16 and the pipe 20 to the motor valve 22. If said valve then is set to deliver the mass through the pipe 24, a circulation of the mass in the ante-chamber is obtained by means of the pumping action, and consequently a levelling out of the heat distribution in the same is obtained. When the mass should be delivered to the processing chamber 8, the motor valve 22 is changed over, whereby the mass is drawn from the ante-chamber and transported out through the pipe 25 to the processing chamber. By means of the pump 18 mass can be drawn from the processing chamber 8 via the inlet pipe 19 and it can subsequently through the motor valve 23 be transported to the processing chamber 8 via the pipe 27. By this arrangement a circulation of the material in the processing chamber by means of the pumping action is possible so that a uniform distribution of the bacteriological culture can be obtained. The circulation by means of the pumping action can alternatively be provided by means of the pump 48 according to FIG. 3. By said circulation the mass is mixed and at the same time the cover of foam, which on top of the mass with the bacteriological culture, and which is impenetrable for the gas, can be broken. When the material shall be removed from the processing chamber, the motor valve 23 is changed over and the material is pressed out through the pipe 26 and further to a collecting station, for example a manure yard. In the variant according to FIG. 3 the mass can be pumped out by pivoting the pump 48 right in front of the pipe 50, as already mentioned.

The transportation means in the embodiment according to FIG. 6 is arranged in the same manner. In the embodiments according to FIGS. 4 and 5 on the other side, only one pumping installation is shown, which can transport mass from the ante-chamber 40 to the processing chamber 41. Excess mass, which may have been supplied, is pressed out from the processing chamber over the edge of the chamber and flows down in the storage space inside the wall 34. However, also these embodiments can be equipped with more complicated transportation means for the circulation in the different spaces by means of the pumping action.

Heat supply, supply of material and removal of the same are adjusted in such a way that the material, before it is removed from the ante-chamber will have a temperature of 60°–70° C. The removal of material from the processing chamber is in its turn so adjusted relative to the supply that the processing chamber contains a considerable quantity of material, preferably not less than ¾ of the available volume. The anaerobic microorganisms, which shall be used for the gas production, are in the mass in the processing chamber, and according to the supply of new mass also this is infiltrated with the bacteriological culture and all supplied mass will successively be subjected to the same and will thereby take part in the gas production.

Said gas production should, as mentioned, take place at the temperature of 55°–60° C., and thus this temperature has to be maintained in the freshly supplied mass in the processing chamber. This is obtained by means of good insulation and a certain quantity of heat being supplied by heat transfer from the mass in the ante-chamber. In order to still further compensate any escape of heat which can vary according to the season, more or less heat can be supplied by means of heat coil, see 31 in FIG. 1. In this connection a regulating system of known type can be used with thermal relays, which register the temperature of the mass and regulate the same.

By means of the bacteriological culture the material is decomposed in the processing chamber 8 and 41 respectively, whereby methane is generated. This gas is taken out in the upper portion of the chamber through the pipe 32 and 39 respectively and is conducted to either one or several kinds of consumption, by way of example heat boilers or gas driven engines and/or to storage spaces for posterior consumption. The gas can be stored at the pressure it gets by the process or be compressed and be stored in pressure vessels.

The material is best utilized for gas production, if this process takes place under mixing of the material. Such a mixing effect is obtained by the stirring action obtained by the circulation of the material by the pumping action described. Supply and removal of material is adjusted so that the average time that the substrate spends in the process approximately amounts to 10 days.

However, in the ante-chamber the time the mass is under treatment is not so important, if it is secured that it reaches the desired temperature. It is most advantageous to work the mass, so that it gets a uniform composition and a levelled out temperature. The best way to achieve this is by mixing. In order to secure a uniform temperature the supply and removal of the material and its circulation by pumping action can take place according to a determined cycle, viz. first the supply and subsequently the circulation by pumping action for a certain period of time, before it is taken out, so that the material supplied will have time to acquire the desired temperature.

When the supplied material is manure, the supply usually takes place once or twice during 24 hours. This material is thus worked by circulation by pumping action in the chamber 7/40 and thereby gets a uniform temperature and a homogeneous consistency. During the warming up and the working action taking place at the same time, certain gases as carbon dioxide may escape depending upon the character of the material. It can be of advantage not to let this gas be mixed with the methane produced. As mentioned, the chamber 7/40 can be closed whereby the gas generated in the chamber easily can be exhausted. The produced methane is taken out from the separated space 8.

By emptying of the space 7/40 into the space 8/41 suitably small quantities will be pumped out consequently at short intervals, approximately once every hour. By this arrangement the bacteriological process is in the least possible way disturbed by newly supplied material. The pumping out of the material from the space 8/41 suitably will occur in the same way, approximately once every hour.

According to the invention the heating of the mass in the ante-chamber serves the purpose to create the intended temperature in the material taking part in the process. However, the heating also has a pasteurizing effect. This effect can be still further increased if the temperature is raised up to and possibly above 65° C., at which temperature pathogenic bacteria of the salmonella family are quickly killed.

However, the material supplied to the gas processing stage should not have a temperature above 65° C. and if pasteurizing effect by increased temperature is desired to obtain the mass supplied for the process a temperature reduction to approximately 60° C. is necessary. This can be effectuated by letting the mass pass through a cooling loop before its infeed and in this connection the emitted heat can be used for preheating of freshly supplied material. It may therefore be of advantage to split up the ante-chamber into zones: one zone for the intake, where the freshly supplied and not heated material is fed to a cooling loop in which the material intended to be delivered to the space 8/41 is transported, and a second zone, which contains a tube loop with a heating medium, to which zone the preheated mass is passed in order to be heated to the desired maximum temperature for its further transportation through said cooling loop to the processing chamber.

Even if the mass is heated in the space 7/40 to above 60° C. it is not sure that any cooling is necessary. By transferring the mass in small quantities to the space 8/41, as has already been mentioned, an insignificant disturbance of the process will arise, even if the quantities supplied should have a temperature above 60° C. The mass will also be cooled during the transportation to the space 8.

By prior art it has been assumed that in bacteriological processes with cultures of anaerobe microorganisms in order to produce methane the temperature should be in the range 30°–40° C. In connection with the present invention it has however, been proved that a production is quite feasible at temperatures between 50°–60° C. At such a temperature the process takes a more rapid course, and therefore the installation can be better utilized than at lower temperatures. However a certain sacrifice has to be made, as the quantity of methane per unit of material will be somewhat less than at the lower temperature. An overall estimate comprising quantity of produced gas and capital costs, however, shows that a process carried through at the higher temperature is more advantageous from an economical point of view. However, in connection with the higher temperature it is important that the temperature is very carefully regulated, so that it will not reach the range of the coagulation temperature of protein, viz. 65° C., which would ruin the bacteriological culture.

Said warming up to a pasteurizing temperature, a minimum of 65° C., is an important phase of the method. Thereby is in fact achieved that the mass of manure produced can be used without the restrictions in force for unpasteurized manure. Thus, the manure can be spread during all seasons and can be used also for horticultural purposes.

The material that has undergone treatment in the process is discharged from the processing chamber and transported to the surrounding manure yard 34, 35 and a separate manure deposit respectively for subsequent use. The material treated in this manner is suitable for use as fertilizer.

INDUSTRIAL APPLICABILITY

In the foregoing it has been described how the plant functions in continuous operation. When starting up the process special measures are, however, required as introductions of the culture of microorganisms in the mass in the processing chamber. For this purpose there are known special methods and additives in order to obtain a secure and quick start of the bacteriological process.

There is a risk that the bacteriological process will cease, and this can occur when the pH-value is incorrect (it should be approximately 6,8), when the temperature is unsuitable (outside of the range of 50°–60° C.), when the mass is exposed to air, when the culture is overloaded (too rapid supply of fresh material), when too much material is removed in each discharge, or when unsuitable ingredients (by way of example chemicals) are supplied to the biological mass. When under such circumstances the process ceases, a new starting up operation is necessary, and this can take place in about the same way as the original one after correction of the sources of faults.

Embodiments of the plant with a compact construction have been mentioned in the description and illustrated in the drawings. In all cases the ante-chamber and the processing chamber thus have been placed in immediate connection to each other. Concentric arrangements or a split up of a common receptacle in the two chambers by means of a horizontal or a vertical wall have been suggested. However, the invention is not limited to such types of arrangements. The invention can also be used by such types of plants, where the ante-chamber and the processing chamber are located separately from each other and/or on separate levels, in which cases they are connected by means of a number of transportation means for the transfer of the substrate. By such arrangements the plant can be adapted to different types of space. By the chambers not being located close to each other, the advantage is obtained that any influence with regard to the temperature between the chambers will not occur.

It is not necessary that the ante-chamber is shaped as a proper receptacle but it can for example comprise a pipe loop or a tubular battery, where the substrate is heated for the purpose indicated. The space for the passage through the pipe or the pipes, thus, constitutes the ante-chamber in such a case.

As has been evident from the description, the receptacle for waste, in which the substrate is collected after having passed the processing chamber, can be separated from the rest of the plant or be integrated in the same as in the embodiments according to FIGS. 4–6. However, the invention is not either in this respect limited to any specific embodiment as the receptacle for waste can have any shape and location or it can be divided up in several spaces. It can also be omitted, if the waste is directly transported away to some kind of loading means for removal.

We claim:

1. A method for the production of methane from a biomass substrate by culture with anaerobic microorganisms in a processing chamber from which the methane is collected, which comprises the steps of:

(a) introducing a fresh supply of organic substrate into an antechamber;

(b) heating said introduced substrate within said antechamber up to at least 70° C.;

(c) mixing and circulating said heated substrate within said antechamber to equalize the temperature throughout said substrate;

(d) cooling portions of said heated substrate by heat exchange with fresh portions of substrate introduced at step (a), to temperatures in the range 50°–60° C. suitable for culturing and growth of said anaerobic micro-organisms;

(e) transferring said so-cooled portions of said substrate to a processing chamber in the presence of a methane-producing anaerobic micro-organism to form a substrate for the culture of said micro-organism contained therein;

(f) maintaining said cultured substrate under anaerobic conditions to promote growth of said micro-organism, until methane is generated; and (g) collecting the generated methane, and discharging from said processing chamber the spent portions of said substrate, converted to fertilizer by the growth of said micro-organism, the rate of transfer of cooled substrate portions from said antechamber to said processing chamber in step (e) being equilibrated to the rate of discharge from said processing chamber in step (g) to maintain optimum growth conditions and substrate volume within said processing chamber.

* * * * *